United States Patent [19]

Kawabe et al.

[11] Patent Number: 5,886,206
[45] Date of Patent: Mar. 23, 1999

[54] PROCESS FOR PRODUCTION OF METHANEDIPHOSPHONIC ACID COMPOUND

[75] Inventors: Norio Kawabe, Kanagawa; Keijiro Takanishi, Shiga; Hiromi Uchiro, Tokyo; Kouichi Tsuruta, Kanagawa; Ryuichi Haruta, Shizouka, all of Japan

[73] Assignee: Toray Industries, Inc., Tokyo, Japan

[21] Appl. No.: 632,421

[22] PCT Filed: Aug. 24, 1995

[86] PCT No.: PCT/JP95/01683

§ 371 Date: Jul. 2, 1996

§ 102(e) Date: Jul. 2, 1996

[87] PCT Pub. No.: WO96/06100

PCT Pub. Date: Feb. 29, 1996

[30] Foreign Application Priority Data

Aug. 24, 1994 [JP] Japan ................................ 6-199443

[51] Int. Cl.⁶ .................................. C07F 9/40; C07F 9/38
[52] U.S. Cl. .............................. 558/161; 560/21; 560/22; 560/23
[58] Field of Search ................... 562/21, 22, 23; 558/161

[56] References Cited

U.S. PATENT DOCUMENTS

| | | | |
|---|---|---|---|
| 5,043,330 | 8/1991 | Nguyen . | |
| 5,128,331 | 7/1992 | Nguyen | 514/101 |
| 5,153,183 | 10/1992 | Kawabe | 514/76 |

OTHER PUBLICATIONS

CA 123:112405 Process for Producing Methane Diphosphate Compounds Takanishi, K. et al WO 9419359 Abstract 1994.

Primary Examiner—Porfirio Nazario-Gonzalez
Assistant Examiner—Jean F. Vollano
Attorney, Agent, or Firm—Birch, Stewart, Kolasch & Birch, LLP

[57] ABSTRACT

A process for production of 1-alkylthiomethanediphosphonic acid compound or 1-arylthiomethanediphosphonic acid compound characterized by removing a thiolate byproduct as an insoluble salt, in the condensation represented by the following formula:

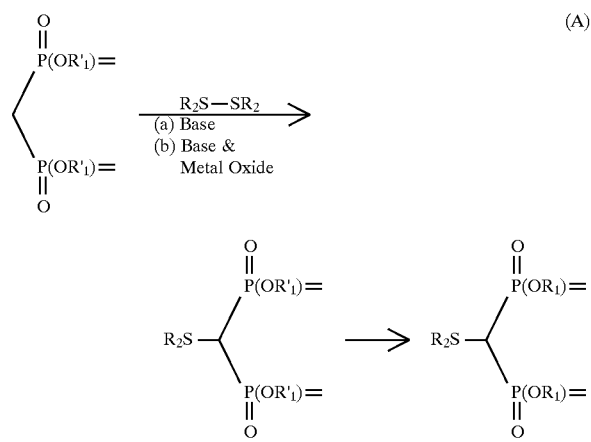

wherein $R'_1$ represents a linear or branched alkyl group having 1 to 6 carbon atoms, $R_2$ represents an alkyl or aryl group, $R_1$ represents a pharmaceutically allowable cation, hydrogen atom, or linear or branched alkyl group having 1 to 6 carbon atoms. The present invention significantly improves the yield compared with conventional methods, and simplifies the purification process at the same time, thus is extremely useful in an economical and industrial points of view.

9 Claims, No Drawings

PROCESS FOR PRODUCTION OF METHANEDIPHOSPHONIC ACID COMPOUND

This application is 371 of PCT/JP95/01683 filed Aug. 24 1995, now WO96/06100.

TECHNICAL FIELD

The present invention relates to a process for production of methanediphosphonic acid compound useful as metal chelating agent, or pharmaceuticals such as anti-inflammatory agent, anti-rheumatic agent, bone-metabolic disease-treating agent and the like.

BACKGROUND ART

A conventional process for synthesis of 1-alkylthio- or 1-arylthiomethanediphosphonic acid is described, for example, in Japanese Examined Patent Publication (Kokoku) No. 4-29676. In the process shown therein, tetraalkyl methanediphosphoniate is converted to a corresponding metal derivative by sodium hydride and the like, and then various disulfides are allowed to react with the derivative to synthesize the objective tetraalkyl 1-alkylthio- or 1-arylthiomethanediphosphonate. Since this synthetic process gives the product in a low yield, a large amount of the recovered disulfide and tetraalkyl methanediphosphonate as well as a byproduct of the reaction, thiol, exist with the objective compound in a crude product, and an industrially expensive purification process, such as silica gel column chromatography, is needed for removing these impurities. Considering the fact that the objective methanediphosphonic acid compounds are highly useful in pharmaceutical fields, the above-mentioned process is not satisfactory to provide a large amount of the compound, and therefore a simple, economical process is required.

The greatest problem in the synthetic process described in Japanese Examined Patent Publication (kokoku) No. 4-29676 is that a large amount of starting material, tetraalkyl methanediphosphonate, was recovered unchanged, resulting in significant labor-consumption for the separation and purification of the objective product from the starting material. If the remaining methanediphosphonate in the reaction mixture can be reduced, this process will be an excellent process for producing 1-alkylthio- or 1-arylthiomethanediphosphonic acid. As the result of detailed investigation of the condensation of tetraalkyl methanediphosphonate with disulfide, the present inventors found that the objective product, tetraalkyl 1-alkylthiomethanediphosphonate or tetraalkyl 1-arylthiomethanediphosphonate, can be obtained in an extremely high yield, by removing the byproduct, alkylthiolate or arylthiolate which is formed in amounts equimolar with the objective product. In addition, it is found that the addition of a metal oxide including magnesium oxide to the synthetic process also provides the objective tetraalkyl 1-alkylthiomethanediphosphonate or tetraalkyl 1-arylthiomethanediphosphonate in a high yield.

Accordingly, it is an object of the present invention to provide a novel process for production of a 1-alkylthiomehanediphosphonic acid compound or 1-arylthiomehanediphosphonic acid compound, which is extremely useful as pharmaceuticals.

DISCLOSURE OF THE INVENTION

The present invention provides a process for production of a methanediphosphonic acid compound represented by the following general formula (1):

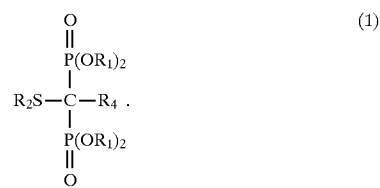

wherein $R_1$ is a pharmaceutically allowable cation, hydrogen atom, or linear or branched alkyl group having 1 to 6 carbon atoms, and may be the same or different, $R_2$ is an alkyl group having 1 to 20 carbon atoms or aryl group having 3 to 20 carbon atoms, and R4 is a hydrogen atom, or linear or branched alkyl group having 1 to 6 carbon atoms; character-zed by reacting a tetraalkyl methanediphosphonate represented by the following formula:

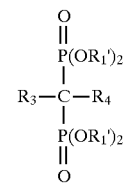

wherein $R'_1$ is a linear or branched alkyl group having 1 to 6, carbon atoms, each $R'_1$ may be the same or different, $R_3$ is a hydrogen, sodium, potassium, or lithium atom, and $R_4$ is the same as above, with a dialkyldisulfide or diaryldisulfide represented by the following formula:

wherein $R_2$ is the same as above; and then removing alkylthiolate or arylthiolate as an insoluble material or an insoluble salt.

BEST MODE FOR CARRYING OUT THE INVENTION

The process for production of a 1-alkylthiomethanediphosphonic acid compound or 1-arylthiomethanediphosphonic acid compound of the present invention is shown in the following reaction formula (A):

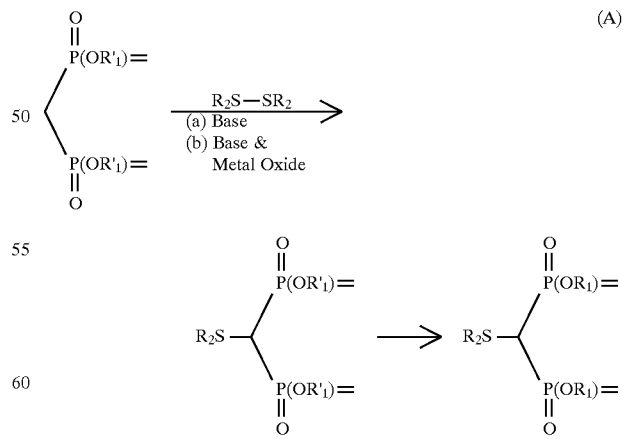

wherein $R'_1$ is a linear or branched alkyl group having 1 to 6 carbon atoms, $R_2$ is an alkyl or aryl group, and $R_1$ is a pharmaceutically allowable cation, hydrogen atom, or linear or branched alkyl group having 1 to 6 carbon atoms. In this process, because the reaction temperature and time varies depending on solvents, reagents, and starting materials used, the conditions described hereinafter are mere preferable features.

As shown in the reaction formula A, the present invention intends to obtain the methanediphosphonic acid compound by reacting tetraalkyl methanediphosphonate with disulfide in the presence of (a) a base or (b) a base and a metal oxide, and then removing the thiolate byproduct as an insoluble salt.

As an example of the present invention, tetraalkyl 1-alkylthio- or 1-aryltbiomethanediphosphonate can be prepared by reacting tetraalkyl methanediphosphonate with disulfide in the presence of a base, and then by removing the thiolate byproduct as an insoluble material or an insoluble salt. When the thiolate is not removed, the yield of the objective tetraalkyl 1-alkylthio- or 1-arylthiomethanediphosphonate significantly decreases, thus the starting materials, i.e. tetraalkyl methanediphosphonate and disulfide are recovered in a large amount. It is important to remove the thiolate from the reaction mixture as an insoluble material or an insoluble salt. The insolubility or solubility of the thiolate depends on the solvent used, the properties of the thiolate itself, the kind of cation which forms a salt with the thiolate.

Elements of the cation are preferably highly ionic elements such as alkaline metals including sodium, potassium, and lithium. These are derived from the base used for the condensation, or separately added to the reaction mixture before or after the condensation.

The suitable solvents for the thiolate salt may include non-polar or slightly polar, aprotonic solvent. Examples of such solvents may include hydrocarbons, such as benzene, toluene, xylene, cyclohexane, hexane and pentane. Between them, slightly polar solvent having a high boiling point, such as toluene and xylene, are preferred.

Since the thiolate salt byproduct precipitates as an insoluble salt in such a reaction mixture, the thiolate byproduct can be almost completely removed from the reaction system or reaction mixture by filtration and the like. The objective compound can be obtained in a high yield by a conventional work up such as extraction, distillation or the like.

Examples of the desirable base used in the present invention may include at least one base selected from the group consisting of hydride, amide, alkyl and alcoholate of alkaline metals or alkaline earth metals. Between them, hydride, amide, alkyl and alcoholate of sodium, lithium, or potassium may be preferably used. Examples of alcoholates may include methylate, ethylate, propylate, and butylate. An alcohol byproduct can be removed from the reaction mixture in advance. The most suitable alcoholate is an alcoholate which is not reactive to the ester exchange reaction, such as potassium t-butoxide. Examples of the bases used may include sodium hydride, sodium amide, lithium amide, methyllithium, butyllithium, potassium t-butoxide, and lithium diisopropylamide.

The content of the base is desirably 2 to 5 equivalent to tetraalkyl methanediphosphonate, the content of the disulfide is desirably 1 to 5 equivalent to tetraalkyl methanediphosphonate. Further, the desired reaction temperature is ranging from −20 ° C. to the boiling point of the solvent used, and desired reaction time is ranging from 1 to 5 hours.

The linear or branched alkyl groups having 1 to 6 carbon atoms, represented as $R_1$, $R_1'$, and $R_4$ in the present invention, may include, but not limited, methyl, ethyl propyl, isopropyl, butyl, isobutyl, s-butyl,t-butyl, pentyl, hexyl, cyclopentyl, methylcyclopentyl, and cyclohexyl group. Groups having a double bond or substituent group, such as halogen, alkoxy, nitrile, amino, ester, benzene ring, may also be included.

Alkyl or aryl groups in the dialkyldisulfide or diaryldisulfide can be arbitrarily selected without limitation. Examples of alkyl groups may include linear, branched, or (hetero)cyclic groups having 1 to 20 carbon atoms, such as methyl, ethyl, propyl, isopropyl, butyl, isobutyl, s-butyl, t-butyl, pentyl, cyclobutyl, cyclopentyl, cyclohexyl, cycloheptyl, and cyclooctyl groups. The alkyl groups may also include groups having a double bond or substituent group, such as halogen, alkoxy, nitrile, amino, ester, and benzene ring. Example of aryl groups may have 3 to 20 carbon atoms, or 3 to 20 carbon atoms and 1 to 3 hetero atoms selected from the group consisting of nitrogen, oxygen, and sulfur. An aryl group having 3, 4 or 5 carbon atoms means the group has 1 to 3 hetero atoms, for example, pyrrole, furan, thiophene, pyridine, thiazole, oxazole, isooxazole, imidazole, pyrazole, pyrimidine, and pyrazine. An aryl group having 6 to 20 carbon atoms means the group consists of only carbon atoms, or both carbon atoms and hetero atoms, for example, phenyl, naphthyl, quinoline, isoquinoline, benzofuran, indole, benzimidazole, benzoxazole, and benzothiazole. These aryl groups may be non-substituted or substituted. Examples of substituted groups may include halogen, alkyl, alkoxy, siloxy, alkylthio, nitro, and amino groups.

Examples of preferred combination of the base with the solvent may include the combinations of potassium t-butoxide, sodium hydride, or n-butyllithium with benzene, toluene, hexane, or cyclohexane.

As another example of the process of the present invention, tetraalkyl 1-alkylthio-or 1-arylthiometllanediphosphonate can be obtained, as shown in reaction formula A(b), by the reaction of a tetraalkyl methanediphosphonate with disulfide in the presence of a base and metal oxide, and then removing an insoluble material including the thiolate salt of the metal oxide and/or thiolate salt. When not removing the thiolate as the insoluble salt, the yield of the objective product will significantly decrease.

The suitable metal oxides used may include magnesium oxide, zinc oxide, and copper oxide, and these combinations. Between them, magnesium oxide is preferred. The content of the metal oxide is 1 to 5 equivalent with tetraalkyl methanediphosphonate.

The tetraalkyl methanediphosphonate, dialkyldisulfide or diaryldisulfide, solvents, bases, and reaction conditions, employed in reaction formula A(a), may also be preferably employed in reaction formula A(b).

The preferred combination of the bases, metal oxides, and solvents may include combinations of bases including potassium t-butoxide, sodium hydride, and n- butyllithium, metal oxides including magnesium oxide, zinc oxide, and copper oxide, and solvents including benzene, toluene, hexane, and cyclohexane.

Among the above-mentioned two methods, A(a) and A(b), the preferably used method is A(a).

The corresponding diphosphonic acid can be obtained by hydrolysis of the resulting tetraalkyl 1-alkylthiomethanediphosphonate or 1-arylthiomethanediphosphonate. The hydrolysis can be accomplished by any known method, for example, by treating the diphosphonate ester with hydrochloric acid at room temperature to 100° C. When using the reaction mixture, obtained the above reaction, of the diphosphonate ester and disulfide, the diphosphonic acid can be easily isolated by extraction or filtration after hydrolysis. Further, the resulting diphosphonic acid can be converted to any salt by any known method.

The cations, which is permissible as $R_1$ of the present invention, represent metallic cations and ammonium ions $N(R_3)_4$, where $R_3$ is a hydrogen atom or a linear or branched alkyl group having 1 to 7 carbon atoms. Preferred metallic cations may include cations of alkaline metals, such as lithium, sodium, and potassium, and of alkaline earth metals, such as magnesium and calcium. Cations of other metals, such as aluminum, zinc, and iron, can, of coarse, be included in the present invention. Ammonium ions may be ammonium ions from ammonia, primary amine compounds, secondary amine compounds and tertiary amine compounds, and quaternary ammonium ions: Examples of ammonium ions may include ammonium ions from ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine, and triethanolamine; and tetraethylammonium and tetraethylammonium. Between them, cations from sodium, potassium, ammonia and alkylamine compounds may be most suitable.

As described above, the process for producing a 1-alkylthio- or 1-arylthiomethanediphosphonic acid compound, characterized by the elimination of an alkylthiolate or arylthiolate byproduct as an insoluble salt, significantly improves the yield compared with conventional methods, and simplifies the purification process at the same time, thus is extremely useful in an economical and industrial points of view.

[EXAMPLES]

The following examples serve to illustrate the present invention, but not to limit the present invention.

Example 1

(4-Methylthiophenyl)thiomethanediphosphonic acid (in General Formula (1), $R_1$=H, $R_2$=4-MeSPh. and $R_4$=H)

A suspension of 1.00 g of potassium tert-butoxide in 10 ml of toluene was refluxed in an atmosphere of argon, and then 1.32 ml of tetraisopropyl methanediphosphonate was added to the suspension, where an azeotropic mixture containing tert-butanol was eliminated by fractional distillation, and toluene was added into the suspension in order to maintain the constant concentration during the reaction. After 30 minutes, a solution of 2.48 g of bis(4-methylthiophenyl)disulfide in 10 ml of toluene was added to the suspension, and the suspension was again refluxed for 4 hours while eliminating tert-butanol by the azeotropic distillation. The resulting solution was cooled to a room temperature, and insoluble materials of the solution were removed by filtration. To the filtrate, 50 ml of 1.5 N hydrochloric acid was added with vigorous stirring. After separation of the organic layer, the water layer was extracted with 10 ml of toluene three times. The organic layer and toluene extract were combined, dried over magnesium sulfate, and evaporated to obtain the tetraisopropyl ester of the title diphosphonic acid as a mixture with disulfide. After the resulting crude ester was refluxed in 20 ml of conc. hydrochloric acid for 5 hours, the resulting aqueous solution is diluted into Price volume with 1.5N hydrochloric acid. The aqueous solution was washed with 8 ml of toluene three times to remove the recovered disulfide, and evaporated to dryness to yield a white solid. Upon recrystallization from acetone/dichloromethane, 1.24 g of the title compound was obtained [yield: 94%, m.p.: 215°–216° C.(dec)]. The resulting white solid was dissolved into water and reacted with sodium carbonate to obtain a disodium compound. The solution was treated with an active charcoal, filtered and concentrated. To the solution was added ethanol. From the ethanol/water solution the disodium salt of the diphosphonic acid (yield: 93%, m.p.: 300° C. or more) crystallized.

$^1$H-NMR of the 2Na salt ($D_2O$.ppm): 2.49(s,3H), 3.23(t, J=20 Hz,1H), 7.25–7.32(m,2H), 7.51–7.58(m,2H)

IR(KBr) of the 2Na salt($cm^{-1}$): 1479, 1197, 1151 1110, 1071, 928

MASS(FAB) of the 2Na salt(m/z): 375 $(M+H)^+$

Elemental analysis: as $C_8H_{10}O_6S_2P_2Na_2$

Calculated: C 25.68%, H 2.70%

Observed: C 25.81%, H 2.75%

Example 2

Tetraisopropyl (4-methylthiophenyl) thiomethanediphosphonate (in General Formula (1), $R_1$=iPr. $R_2$=4-MeSPh, and $R_4$=H)

By a method similar to EXAMPLE 1, condensation was carried out by using 9.00 g of potassium tert-butoxide, 13.5 g of tetraisopropyl methanediphosphonate, and 12.5 g of bis(4-methylthiophenyl)disulfide. After filtration of insoluble material, 19.5 g of title crude product was obtained as pale yellow oil after similar treatment of the filtrate. The purity of the crude product was 95% according to HPLC analysis, and the yield of the title product was 92.6%.

Example 3

Tetraisopropyl (4-Methylthiophenyl) thiomethanediphosphonate (in General Formula (1), $R_1$=iPr $R_2$=4-MeSPh and $R_4$=H)

In an argon atmosphere, a suspension of 13.7 g of bis(4-methylthiophenyl)disulfide and 9.43 g of potassium tert-butoxide in 120 ml of toluene was heated to 50 ° C., and then 13.8 g of tetraisopropyl methanediphosphonate was added to the suspension, and heated to 70 ° C. for one hour. After cooling of the suspension to a room temperature, the precipitate was filtered off and washed with 100 ml of toluene, which was combined with the filtrate. The filtrate combined with the wash toluene was washed with 40 ml of 2N hydrochloric acid three times, and the solvent was evaporated. The title product (20.9 g) was obtained as a crude product. The purity of the product by HPLC analysis was 89.4%, and the yield was 93.6%.

Example 4

Tetraisopropyl (4-Methylthiophenyl) thiomethanediphosphonate (in General Formula (1). $R_1$=iPr, $R_2$=4-MeSPh, and $R_4$=H)

In an argon atmosphere, a suspension of 13.8 g of tetraisopropyl methanediphosphonate and 13.7 g of bis(4-methylthiophenyl)disulfide in 120 ml of toluene was cooled to 0°–10° C., and then 9.43 g of potassium t-butoxide was added to the suspension, and the suspension was allowed to react for one hour. After the treatment of the resulting solution according to EXAMPLE 3, 21.3 g of the title compound was obtained as a crude product. The purity by HPLC analysis was 91.5% and the yield was 97.6%.

Example 5

(4-Methylthiophenyl)thiomethanediphosphonic acid (in General Formula (1), $R_1=H, R_2=4$-MeSPh and $R_4=H$) [A Method using Magnesium Oxide as a Metal Oxide]

In an argon atmosphere, a suspension of 0.99 g of potassium tert-butoxide and 0.48 g of magnesium oxide in 10 ml of toluene was refluxed, and then 1.32 ml of tetraisopropyl methanediphosphonate was added into the suspension. The tert-butanol was separated as azeotropic mixture by a fractionating apparatus and toluene was added to the reaction mixture in order to maintain the initial concentration during the reaction. After reflux for 30 minutes, a solution of 2.48 g of bis(4-methylthiophenyl)disulfide in 10 ml of toluene was added to the reaction mixture. Then, the mixture was refluxed for four hours white removing tert-butanol by azeotropic distillation. After cooling of the mixture to a room temperature, the insoluble solid material including magnesium oxide was filtered out. Into the filtrate was added 50 ml of 1.5N hydrochloric acid with vigorous stirring. The organic layer was isolated and the water layer was extracted with 10 ml of toluene three limes. After the organic layer combined with the extract was dried over magnesium sulfate and the solvent was evaporated, the tetraisopropyl ester of title compound was obtained as a mixture with disulfide. After the crude product was refluxed in 20 ml of conc. hydrochloric acid for 5 hours, the resulting aqueous solution was diluted to twice with 1.5N hydrochloric acid. The aqueous solution was washed with 8 ml of toluene three times to remove the remaining disulfide, and concentrated to dryness to obtain a white solid material. Upon recrystallization of this material from acetone/dichloromethane, 1.23 g of the title compound was obtained (yield of 93%, m.p. of 215°–216° C. (dec)). The resulting white solid material was dissolved into water and reacted with sodium carbonate to obtain a disodium compound. After being treated with an active charcoal, filtered and concentrated, the solution was mixed with ethanol. From the ethanol/water solution the disodium salt of the diphosphonic acid (yield: 93%, m.p.: 300 ° C. or more) crystallized.

MASS (FAB) of disodium salt: m/z=375 $(M+H)_+$.

Elemental Analysis: as $C_8H_{10}O_6S_2P_2Na_2$

Calculated: C 25.68%, H 2.70%

Observed: C 25.71%, H 2.73%

Example 6

(4-Methylthiophenyl)thiomethanediphosphonic acid (in General Formula (1) $R_1=H, R_2=4$-MeSPh, and $R_4=H$) [A Method using Zinc Oxide as a Metal Oxide]

By using of 0.98 g of zinc oxide instead of magnesium oxide in EXAMPLE 5 and treating in a similar manner, the title compound was obtained in the yield of 90%.

Example 7

(4-Methylthiophenyl)thiomethanediphosphonic acid (in General Formula (1), $R_1=H, R_2=4$-MeSPh. and $R_4=H$) [A Method using Copper Oxide as a Metal Oxide]

By using of 0.95 g of copper oxide instead of magnesium oxide in EXAMPLE 5 and treating in a similar manner, the title compound was obtained in the yield of 85%.

Example 8

(4-chlorophenyl) thiomethanediphosphonic acid (in General Formula (1) $R_1=H$, $R_2=4$-Cl-Ph, and $R_4=H$)

By using of 4,4'-dichlorodiphenyldisulfide as a starting disulfide and treating in a manner similar to EXAMPLE 5, the title compound was obtained in the yield of 92%.

Elemental Analysis: as $C_7H_7O_6ClSP_2Na_2$

Calculated: C 23.19%, H 1.95%

Observed: C 23.22%, H 1.93%

Comparative Example 1

Tetraisopropyl (4-Methylthiophenyl) thiomethanediphosphonate (in General Formula (1), $R_1=iPr. R_2=4$-MeSPh, and $R_4=H$)

By applying the same procedure as EXAMPLE 2 except that thiolate was not filtered out as the insoluble material, the resulting crude product including the title compound was obtained. After purification with column chromatography, 13.20 g of title compound was obtained as pale yellow oil. The yield was 65%.

INDUSTRIAL APPLICABILITY

Since the process for production of 1-alkylthiomethanediphosphonic acid compound or 1-arylthiomethanediphosphonic acid compound, which is characterized by removing alkylthiolate or arylthiolate as an insoluble salt, significantly improves the yield compared with conventional methods, and simplifies the purification process at the same time, thus it is extremely useful in an economical and industrial points of view.

We claim:

1. A process for production of a methanediphosphonic acid compound represented by the following general formula (1):

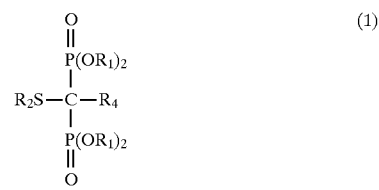

wherein $R_1$ is a pharmaceutically allowable cation, hydrogen atom, or linear or branched alkyl group having 1 to 6 carbon atoms, and may be the same or different, $R_2$ is an alkyl group having 1 to 20 carbon atoms or an aryl group having 3 to 20 carbon atoms, and $R_4$ is a hydrogen atom, or linear or branched alkyl group having 1 to 6 carbon atoms; comprising:

reacting a tetraalkyl methanediphosphonate represented by the following formula:

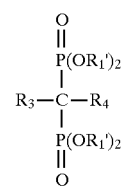

wherein $R_1'$ is a linear or branched alkyl group having 1 to 6 carbon atoms, and may be the same or different, $R_3$ is a hydrogen, sodium, potassium, or lithium atom, and $R_4$ is the same as above, with a dialkyldisulfide or diaryldisulfide represented by the following formula:

$$R_2S\text{—}SR_2$$

wherein $R_2$ is the same as above, in the presence of a base;

removing alkylthiolate or arylthiolate as an insoluble material or an insoluble salt out of the reaction mixture;

then adding aqueous solution to obtain the resulting diphosphonate ester; and recovering a methanediphosphonic acid compound product.

2. A process for production of a methanediphosphonic acid compound described in claim 1, wherein both $R_3$ and $R_4$ are hydrogen atoms.

3. A process for production of a methanediphosphonic acid compound described in claim 2, wherein the reaction is carried out in the presence of a base and a metal oxide.

4. A process for production of a methanediphosphonic acid compound described in claim 3, wherein the metal oxide is at least one oxide selected from the group consisting of magnesium oxide, zinc oxide and copper oxide.

5. A process for production of a methanediphosphonic acid compound described in claim 3, wherein the metal oxide is used by 1 to 5 equivalents to tetraalkyl methanediphosphonate.

6. A process for production of a methanediphosphonic acid compound described in claim 2, wherein the base is at least one base selected from the group consisting of hydride, amide, alkyl and alcoholate of alkaline metals and alkaline earth metals.

7. A process for production of a methanediphosphonic acid compound described in claim 2, wherein the base is used by 2 to 5 equivalents to tetraalkyl methanediphosphonate.

8. A process for production of a methanediphosphonic acid compound described in claim 2, wherein a non-polar or low-polar aprotonic solvent is used as a reaction solvent.

9. A process for production of a methanediphosphonic acid compound described in claim 2, wherein the reaction temperature is from −20° C. to the boiling point of the solvent.

* * * * *

UNITED STATES PATENT AND TRADEMARK OFFICE
CERTIFICATE OF CORRECTION

Page 1 of 2

PATENT NO. : 5,886,206

DATED : March 23, 1999

INVENTOR(S) : Norio KAWABE et al.

It is certified that error appears in the above-identified patent and that said Letters Patent is hereby corrected as shown below:

Title page,
item [57], the Abstract, after line 6, and at col. 2, lines 40-63, please delete all of the formulas and insert in place thereof the following correct formulas:

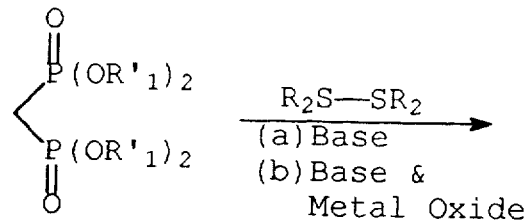

(A)

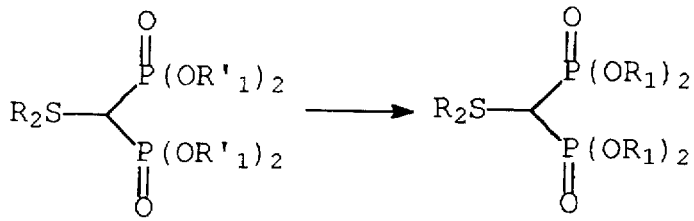

At col. 2, line 13, change "R4" to --$R_4$--

At col. 2, line 15, change "chacter-zed" to --characterized--

At col. 2, line 27, after "6" delete the comma

UNITED STATES PATENT AND TRADEMARK OFFICE
CERTIFICATE OF CORRECTION

PATENT NO. : 5,886,206
DATED : March 23, 1999
INVENTOR(S) : Norio Kawabe, et. al.

It is certified that error appears in the above-identified patent and that said Letters Patent is hereby corrected as shown below:

At col. 4, line 35, change "1-arylthiometllanediphosphonate" to --1-arylthiomethanediphosphonate--

At col. 5, line 23, change "tetraethylammonium" to --tetramethylammonium--

At col. 5, line 66, change "Price" to --twice--

Signed and Sealed this

Thirtieth Day of November, 1999

Attest:

Q. TODD DICKINSON

Attesting Officer

Acting Commissioner of Patents and Trademarks